United States Patent
Saint-Germain

Patent Number: 5,873,495
Date of Patent: Feb. 23, 1999

[54] DEVICE FOR DISPENSING MULTI-COMPONENTS FROM A CONTAINER

[76] Inventor: Jean G. Saint-Germain, 54 Fredrick St., 2nd Fl., Stamford, Conn. 06902

[21] Appl. No.: 754,703

[22] Filed: Nov. 21, 1996

[51] Int. Cl.$^6$ .............................. B67D 5/52; B67D 1/07; B67D 5/56
[52] U.S. Cl. .................... 222/135; 222/129; 222/192; 222/390
[58] Field of Search ................... 222/132, 135, 222/390, 192, 93, 106

[56] References Cited

U.S. PATENT DOCUMENTS

| | | | |
|---|---|---|---|
| 4,865,481 | 9/1989 | Scales | 401/195 |
| 5,228,595 | 7/1993 | Booker | 222/179.5 |
| 5,346,097 | 9/1994 | Melland et al. | 222/132 |

FOREIGN PATENT DOCUMENTS 0369722  8/1993  European Pat. Off. .

Primary Examiner—Andres Kashnikow
Assistant Examiner—Keats Quinalty

[57] ABSTRACT

A multi-chambered tooth care dispensing device and more particularly, to a device that dispenses toothpaste, mouthwash and dental floss all from one convenient package. The toothpaste and the mouthwash are stored in side by side chambers and the dental floss is stored in the lower portion of the dispensing package and is led through a top opening that is provided with a floss cutting knife to allow the user to cut the floss to the desired length. The toothpaste and the mouthwash is delivered by hand action of a three way finger switch connected to a one-way set of gears and screw auger each connected to a piston. This forces the contents of each chamber up and out of the delivery outlet. The three-way hand/finger operated switch may be set to toothpaste in one direction and to mouthwash in the other direction with an off position in between. The device is provided with a meter in the lower end to indicate the amount of floss remaining and the body of the device has two windows that displays the percentage of toothpaste and the ounces of mouthwash remaining that allows the user to see the amount of toothpaste and mouthwash that is remaining. A storage area is provided in the device for toothbrush storage. The exit port for the toothpaste, is a stylized pentagon in shape which forms the same shape of the toothpaste. This shape makes the toothpaste considerably more stable on the brush.

6 Claims, 5 Drawing Sheets

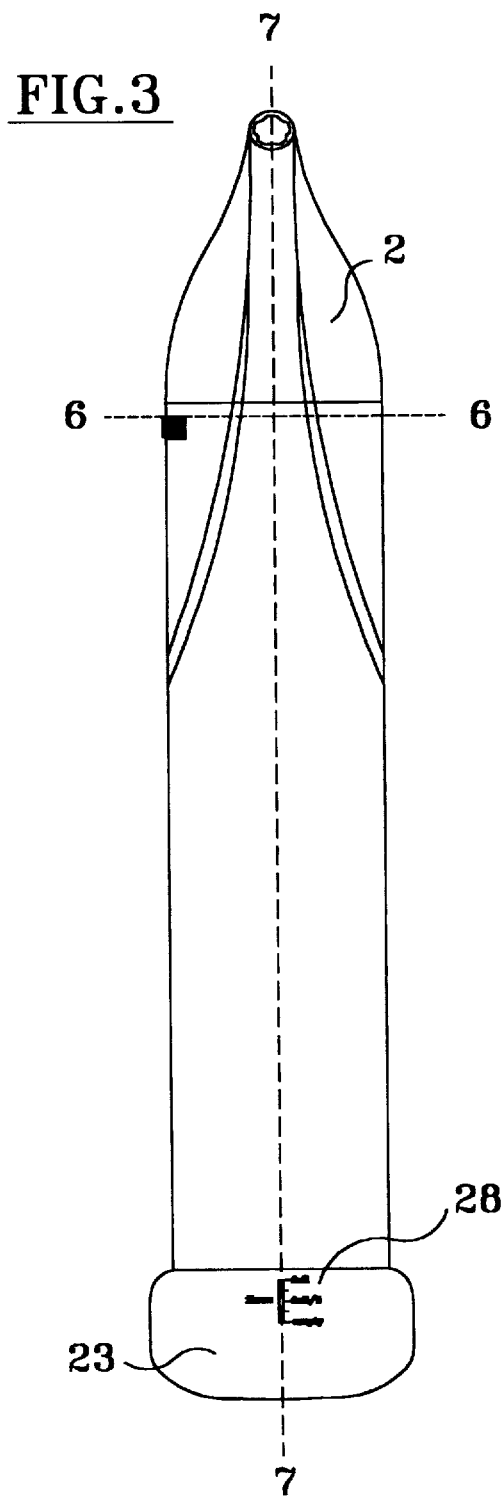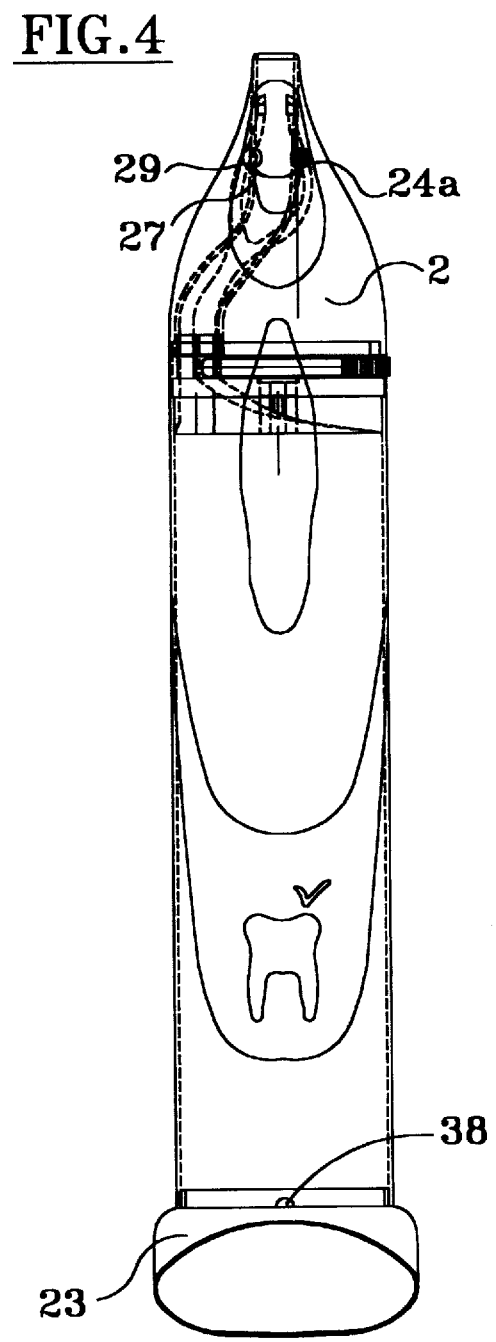

DEVICE FOR DISPENSING MULTI-COMPONENTS FROM A CONTAINER

FIELD OF THE INVENTION

The field of the present invention is dispensing device for dental products.

BACKGROUND OF THE INVENTION

The following U.S. Patents relate to the dispensing of both singular pasty products from a delivery container or the delivery of such pasty products in a two or multi-product from a delivery container. However, none of the cited patents disclose or even suggest the novel concept of the present invention which is combining a delivery device that can deliver toothpaste, mouthwash and dental floss from one convenient delivery package:

U.S. Pat. No. 2,914,220 issued to L. L. Marrafino, et al. on 24 Nov. 1959, entitled Striping Dispenser and discloses a striping device for placing strips on tooth paste as it is being squeezed out of the container. There is no showing of a multi-product dispensing device for toothpaste, mouthwash and dental floss.

U.S. Pat. No. 3,135,428 issued to John Gallo on 02 Jun. 1964, entitled Dispensing Device and discloses a dispensing device having its primary object providing a nozzle for dispensing multi-colored pastelike substances in predetermined arrangements or designs. There is no showing or suggestion of a multi-product dispensing device for toothpaste, mouthwash and dental floss.

U.S. Pat. No. 3,747,804 issued to H. Raaf, et al. on 23 Jul. 1973, entitled DEVICE FOR SIMULTANEOUSLY DISPENSING DIFFERENT MATERIALS FROM A CONTAINER and discloses a device for simultaneously dispensing different materials from the same container. There is no showing or suggestion of a multi-product dispensing device for toothpaste, mouthwash and dental floss.

U.S. Pat. No. 4,438,871 issued to Josef Eckert on 27 Mar. 1984, entitled DISPENSER and discloses a dispenser for pasty substances with two metering pistons arranged coaxially. There is no showing or suggestion of a multi-product dispensing device for toothpaste, mouthwash and dental floss.

U.S. Pat. No. 4,804,115 issued to M. F. Ball on 14 Feb. 1989, entitled PUMP CHAMBER DISPENSER and discloses a pump chamber for striping its contents. There is no showing or suggesting of a multi- product dispensing device for tooth paste, mouthwash and dental floss.

U.S. Pat. No. 4,821,926 issued on 18 Apr. 1989, entitled DISPENSER OF PASTE-LIKE PRODUCTS, IN PARTICULAR TOOTHPASTE and discloses a single generic toothpaste product dispenser. There is no showing or suggestion of a multi-product dispensing device for toothpaste, mouthwash and dental floss.

U.S. Pat No. 4,846,372 issued to A. von Schuckmann on 11 Jul. 1989, entitled DISPENSER FOR PASTE COMPOSITIONS and discloses a multi-component toothpaste pump dispenser that utilizes delivery tube extending below the reservoir striping paste and into the reservoir of main paste. There is no showing or suggestion of a multi-product dispensing device for tooth paste, mouthwash and dental floss.

U.S. Pat No. 4,927,059 issued to Fiedler et al. on 22 May 1990, entitled DEVICE FOR DISPENSING A MULTI-COMPONENT FLOWABLE SUBSTANCE and discloses a device for dispensing a striped mixture of paste-like flowable substance, such as toothpaste, which includes a lower container in which one of the components is retained. There is no showing or suggestion of a multi-product dispensing device for toothpaste, mouthwash and dental floss. There is no showing or suggestion of a multi-product dispensing device for toothpaste, mouthwash and dental floss.

U.S. Pat. No. 4,979,646 issued to R. Andris on 25 Dec. 1990, entitled PASTE DISPENSER and discloses a paste dispenser including a pump for dispensing metered amounts of pasty substances, such as toothpaste or the like, from bottle-like or can-like containers which have a bellows made of an elastic material. There is no showing or suggestion of a multi-product dispensing device for toothpaste, mouthwash and dental floss.

U.S. Pat. No. 5,027,981 issued to H. Magister on 02 Jul. 1991, entitled DISPENSER CARTRIDGE FOR TWO COMPONENT SYSTEM and discloses a cartridge containing two components of a two component system wherein the two components have substantially balanced degrees of compressibility and in a predetermined ratio. There is no showing or suggestion of a multi-product dispensing device for toothpaste, mouthwash and dental floss.

U.S. Pat. No. 5,038,963 issued to Pettengill, et al. on 13 Aug. 1991 entitled DEVICE FOR DISPENSING TWO DIFFERENT MATERIALS FROM CONTAINER AT SAME TIME and discloses a container for the co-extrusion at least two flowable materials, each having an outlet passage for said materials and being extruded at the same time. There is no showing or suggestion of a multi-product dispensing device for toothpaste, mouthwash and dental floss.

While all of the above cited Patents are in the field of dispensing toothpaste and some disclose devices that store and dispense multiple materials, none of them discloses or even suggests the novel dispensing device of the present invention, wherein a user has a single container that supplies him with toothpaste for brushing his teeth with a toothbrush that may be stored in the dispenser container of the present invention, then by self selection he can spray mouthwash into his mouth from said same dispensing container and when he has brushed and cleaned his breath with mouthwash he is able to pull a string of dental floss from said same dispensing container and cut it off at the desired length with the cutting knife provided on said dispensing container.

OBJECTS OF THE PRESENT INVENTION

An object of the present invention is to provide a dispensing device for the consumer that provides said consumer with a single device that can deliver the three daily dental hygiene needs all in one dispenser, namely, toothpaste, mouthwash and dental floss.

Another object of the present invention is to provide a single dispensing device for the traveler, thereby eliminating the need to pack three different dental hygiene products when traveling.

A further object of the present invention is to provide space saving in a bath room by eliminating the need for three different dental hygiene products in a medicine cabinet or on the sink.

Various other objects, advantages and features of the present invention will become apparent to those skilled in the art when they study the previous and the following discussions, taken in conjunction with the drawings, which constitute a part hereof.

SUMMARY OF THE PRESENT INVENTION

There are many modern dental product dispenser that have replaced the old time toothpaste tube. However, multi-product dispensing devices have been limited to very few such as toothpaste and mouthwash but none have delivered complete dental care until the present invention which delivers toothpaste, mouthwash and dental floss, with storage space for a toothbrush. The device of the present invention is operated by hand. There are three by side chambers, one for toothpaste, one for mouthwash and the third to store the user's toothbrush. There is a separate cavity for a spool of dental floss that allows the floss to be led to the ear opening of the penguin shaped container used for the present invention. Said floss is pulled out of said ear and led over to the knife edge for cutting to the desired length. The toothpaste may be of any conventional type and the mouthwash may be any liquid mouthwash. The dental floss may be the well known string-type or the newly developed brush type, having one or more different size brushes, especially for people with various spaces between their teeth. Such brushed dental floss is described in U.S. Pat. No. 5,316,028 issued to Patricia S. Flemming of Greenwich, Conn., entitled DENTAL FLOSS AND DEVICE FOR DISPENSING, issued 31 May 1994. The Flemming Patent discloses a system, wherein the floss is pre-marked with a color, so that the user knows just where to cut the floss for use, thereby saving money by eliminating wasted floss. The device of the present invention operates by a three position thumb switch. When the user wishes to extract toothpaste he moves the thumb switch in the paste direction and rotates the belt driver in one direction to activate the augured piston at the bottom of the paste chamber to drive the product out the delivery port of the penguin styled container. When the user wishes to use mouthwash, he moves the thumb switch to the opposite end for the mouthwash position. As described above, to obtain mouthwash, he places the delivery port in front of his mouth and continually moves the friction belt of the switch that will cause the mouthwash to be sprayed in his mouth by the action of the water proof augured piston in the mouthwash chamber. The amount of toothpaste and mouthwash is displayed on film strips that are pulled out of small windows at the base of the two toothpaste and mouthwash chambers. The strip for the toothpaste indicates the percentage of toothpaste remaining in the chamber, the strip for the mouthwash indicates the ounces of mouthwash remaining in the chamber. The strips operate as the pistons rise and the strips are led back inside the body of the dispenser through another small set of windows above the exit windows. The entrance windows above the exit windows leave enough space so that the percentage and ounce indications are visible. The lower potion of the device is provided with a meter so that the user may be aware of the amount of dental floss left on the internal spool. The exit port for the toothpaste is specifically shaped as a stylized pentagon. This shape forces the extruded toothpaste to exit in that stylized pentagon shape. The advantage of this shape is that it maintains the toothpaste on the toothbrush much more stable than a round shape that tends to roll off the toothbrush.

BRIEF DESCRIPTION OF THE DRAWINGS

FIG. 3. is a front view of the dispensing container of the present invention.

FIG. 4. is a broken back view of the dispensing container of the present invention.

DETAILED DESCRIPTION OF THE PREFERRED EMBODIMENTS

Figure 1:
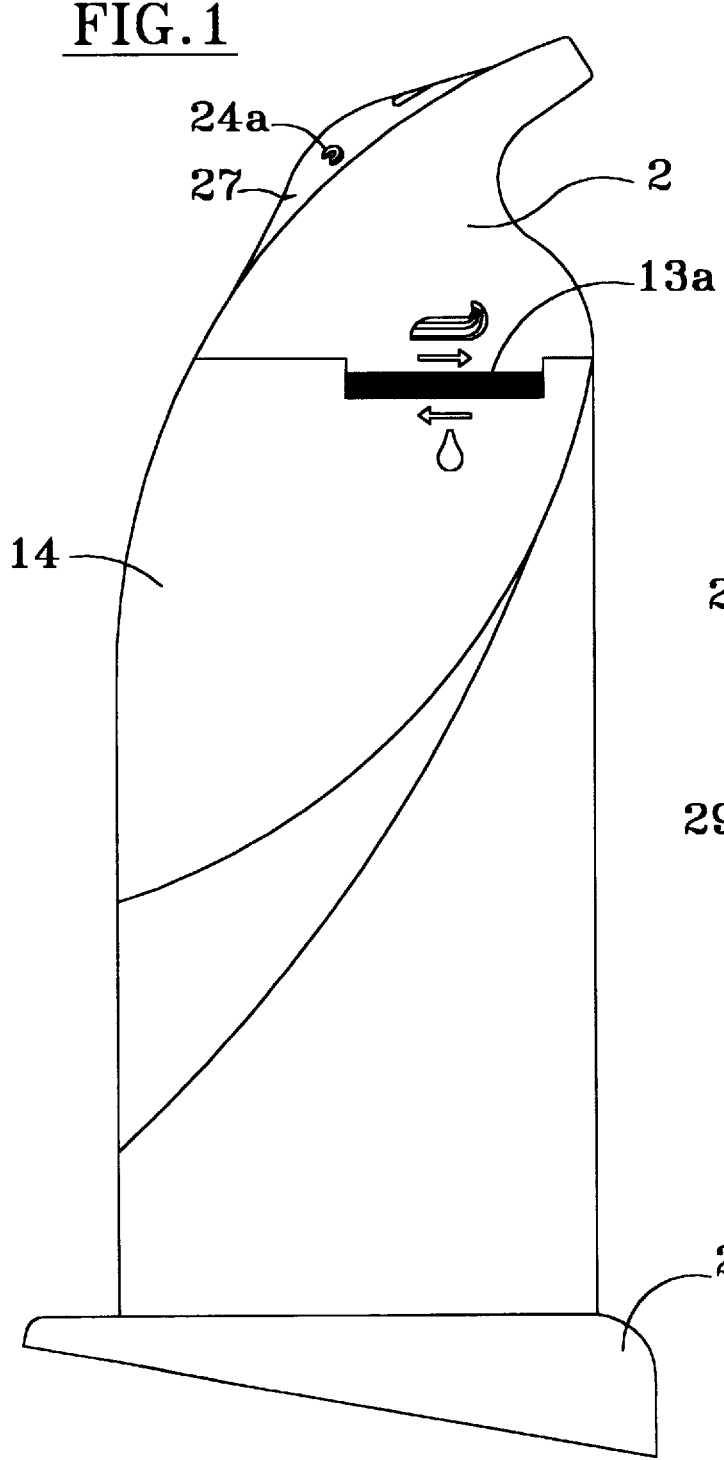
FIG. 1. is a side view of the right side of the dispensing container of the present invention.
Figure 2:
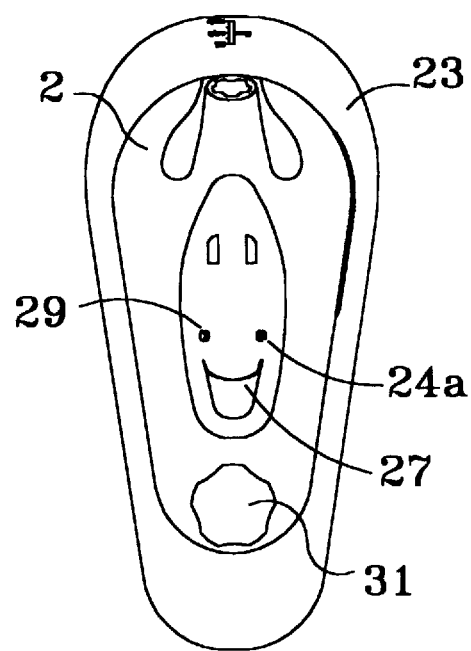
FIG. 2. is a top view of the dispensing container of the present invention.
Figure 5:
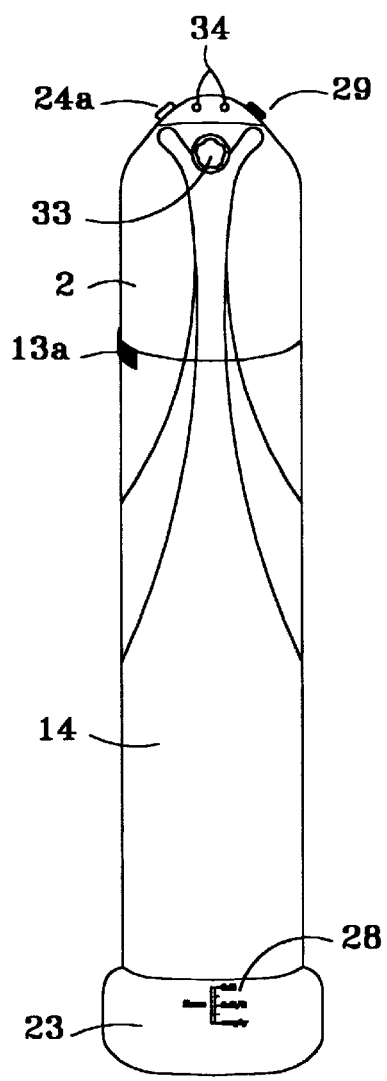
FIG. 5. is a front perspective view of the dispensing container of the present invention.
Figure 6:
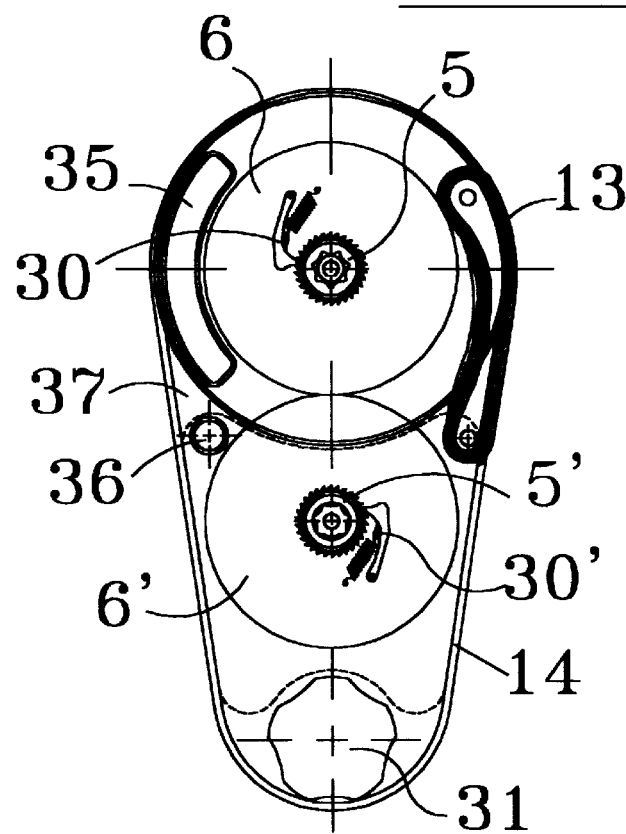
FIG. 6. is a section taken on along the line 6—6 of FIG. 3.
Figure 7:
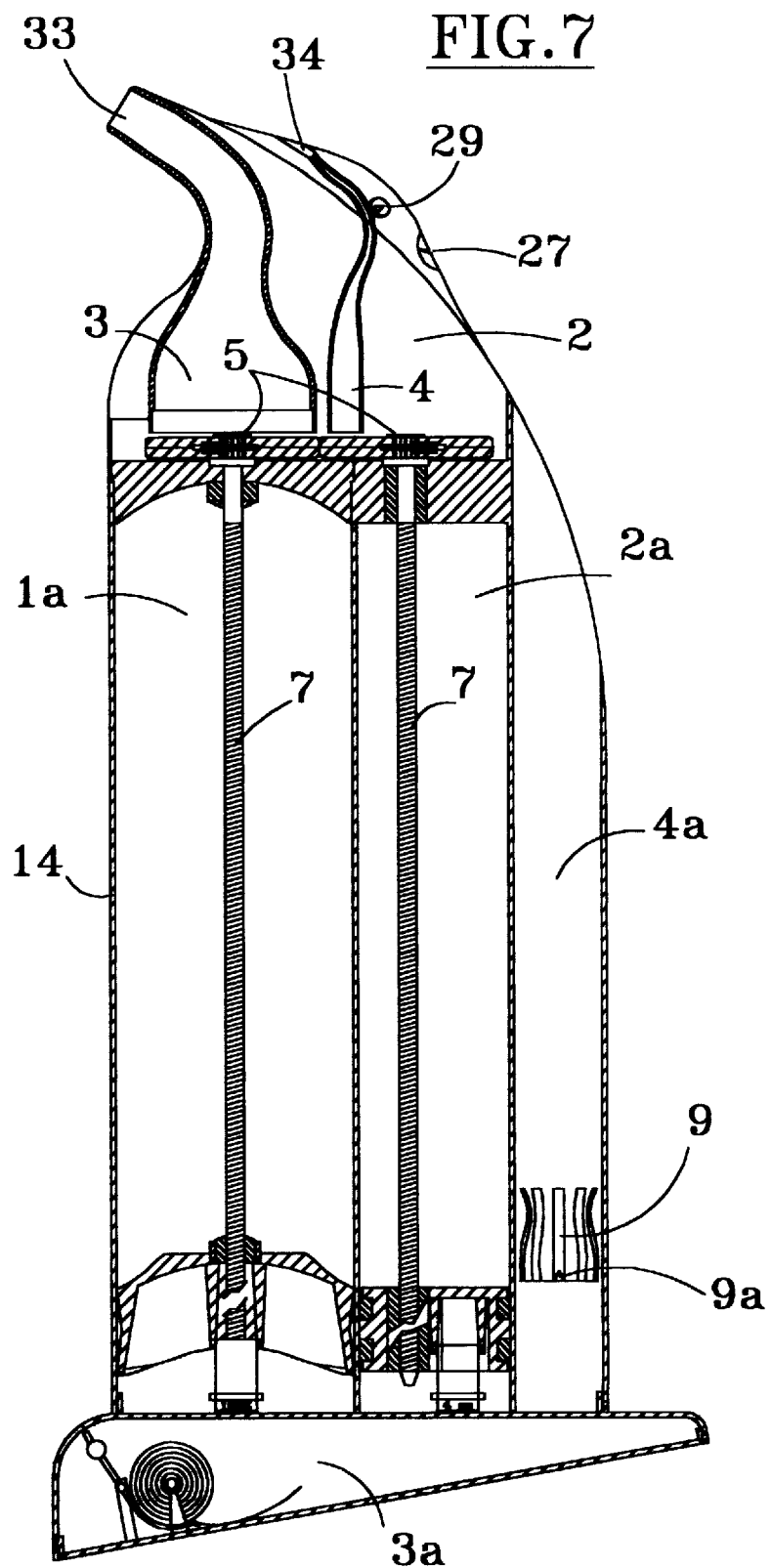
FIG. 7. is a section taken along the line 7—7 of FIG. 3.
Figure 8:
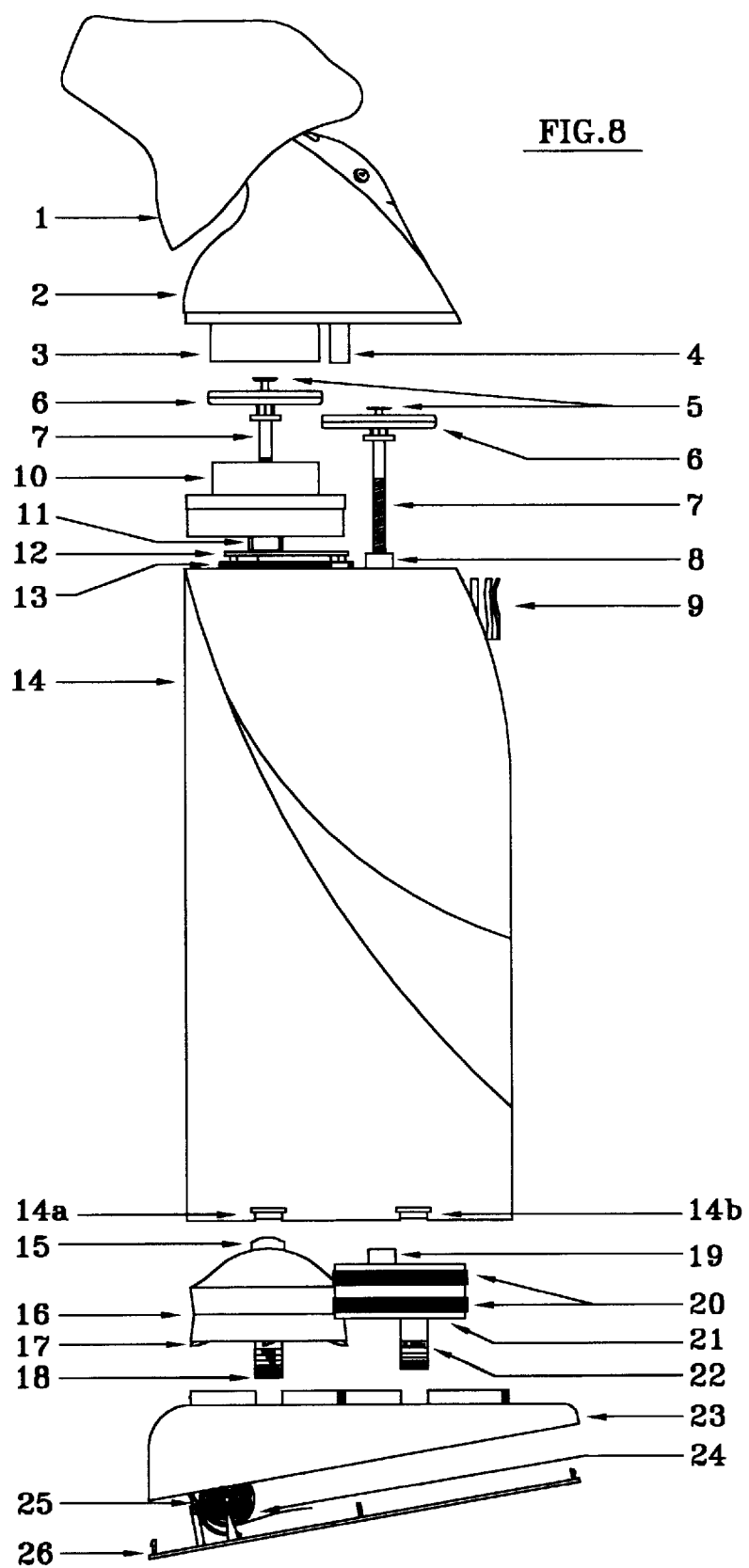
FIG. 8. is a broken view of the dispensing container of the present invention.

The multi-dental product dispensing container of the present invention shown in the drawings includes four separate housing parts, each of which is for a different dental product, 1a for toothpaste, 2a for mouthwash, 3a for dental floss and 4a for the toothbrush storage area. The entire container, other than the various gaskets, is made of dimensionally stable material such as plastic. In FIG. 8 the cover cup that is used to keep the products to be dispensed fresh and may also be used as a liquid container is shown at 1. The dispensing head is at 2, the toothpaste dispensing tubing is at 3 and the mouthwash tubing is at 4. The friction gears 6 are topped with gear caps 5 and operate the gear screw augers 7 Mouthwash fluid sealant "O" ring is at 8, toothbrush internal storage entrance and retainer is at 9, the toothpaste static piston is a 10 and sealant is at 11. 12 is the friction belt retainer and 13 is the friction belt that operates the screw augers 7 by continuous movement of three-way switch shown in FIG. 1 at 13a. The multi-product container housing is at 14. The toothpaste movable piston is at 16 and the sealant is at 15 with the toothpaste meter is at 18. On the other side is the Mouthwash piston at 21, the "O" ring sealant at 20, the piston sealant at 19 and the mouthwash meter at 22. Just below the toothpaste and mouthwash auger operated pistons is container 14 bottom and cover 23. In said bottom cover 23 is stored the spool of dental floss 24 that has a spool-contents gage 25, as shown in FIG. 3 that measures the depth of the contents. The floss spool 24 is seen through floss depth display 28. Floss accessory platform 26 snaps into bottom cover 23. The floss 24a is led through an internal passage of the housing 14 to the dispenser head 2 and out the penguin's ear On the lower end of dispensing container is a set of windows 14a for the percentage of tooth paste remaining in its chamber and 14b for the number of ounces of mouthwash remaining in its chamber. Said floss 24 is led through leader slit 27 to cutter 29, as shown in FIG. 5. In FIG. 6, the view taken on line 6—6 of FIG. 3. The toothpaste exits through exitway 33, which is a stylized pentagon in shape to make the extruded toothpaste on a toothbrush more stable, by way of passageway 35 and the mouthwash exits through exitway 34 by way of passageway 36, as shown in FIGS. 6 & 7, by the action of the toothpaste piston 16, which is stabilized by non-rotational damper 16a and the mouthwash exits by the action of the piston 21 when switch 13a is set for either toothpaste or mouthwash and friction belt is moved in the proper direction. No such non-rotational damper is required for piston 21.

In order to more clearly understand the internal operation of the device of the present invention, reference is now made to FIG. 6, wherein the housing of the dental product dispensing device of the present invention is shown on line 6—6, of FIG. 3, the friction gear for the toothpaste is at 6 and at 6' for the mouthwash, the gear caps are at 5 and 5', in the same manner, the one-way gear locks are at 30 and 30', the toothbrush cavity is at 31 with the brush storage basket at 9 and 16 toothbrush storage basket retainer 9a as shown in FIG. 7.

The dental floss is led up through the space 37 between the toothpaste and mouthwash containers 1a and 2a and out through as shown in FIG. 7. to the opening 24*a* in device cap 2 and led through slit 27 to cutter 24*b*. This arrangement allows the floss end to remain available to be pulled out to the desired length for the next use.

While the description supra., contains many specificities, the reader should not construe these to be limitations on the scope of the invention, but merely as exemplifications of a preferred embodiment of the present invention. Those skilled in the art will envision that many other possible variations are within the scope of the present invention. For example, skilled artisans will readily be able to change the dimensions and the materials of the various embodiments. They can make many variations on the design of the present invention. Accordingly, the reader is requested to determine the scope of the present invention only by the scope of the appended claims and their legal equivalents, taken in view of the scope of this specification, and not by the examples that have been given herein.

What I claim is:

1. A multi-dental product dispenser comprising first, second cylindrical storage housing areas and a third storage area; said first storage housing area provided to store toothpaste for dispensing; said second storage housing area to store mouthwash dispensing mouthwash; said first and second storage areas arranged in a side-by-side position; said third storage provided for the dispensing of straight or brushed dental floss and is provided below said first and second areas; said first, second and third storage area, along with the dispensing area provided above said storage areas, said dispensing area comprises a dispensing cap having 3 dispensing exit openings, one for toothpaste, one for mouthwash and one for straight or brushed dental floss; the lower portion of said dispenser provided with a three way position selection switch friction belt, the forward position for moving the friction belt portion of said friction belt that dispenses toothpaste, the center position for "off" and the rear position for dispensing mouthwash by the moving of the friction belt in the opposite direction, thereby forcing the toothpaste and mouthwash by pistons located at the base of said first and second cylindrical storage area, out the dispensing exits provided in said dispensing cap; said third dispensing area provided with dental floss that is dispensed through a third exit in said dispensing cap.

2. The multi-dental product dispenser of claim 1 wherein said dispensing of said toothpaste and mouthwash is accomplished by continuous one direction movement of said friction belt.

3. The multi-dental product dispenser of claim 1 wherein said dental floss is straight dental floss.

4. The multi-dental product dispenser of claim 1 wherein said dental floss is pre-cut marked brushed floss.

5. The multi-dental product dispenser of claim 1 wherein said dispenser is provided with meters to report on the remaining products of toothpaste, mouthwash and dental floss.

6. The multi-dental product dispenser of claim 1 wherein said dispenser is provided with a toothbrush storage area, wherein said storage area is provided with a draining means to accomodate drainage from a stored toothbrush.

* * * * *